United States Patent [19]

Kuroda et al.

[11] Patent Number: 5,384,189
[45] Date of Patent: Jan. 24, 1995

[54] WATER-DECOMPOSABLE NON-WOVEN FABRIC

[75] Inventors: Hideo Kuroda; Yasunori Sakamoto, both of Kanagawa, Japan

[73] Assignee: Lion Corporation, Tokyo, Japan

[21] Appl. No.: 9,760

[22] Filed: Jan. 27, 1993

[51] Int. Cl.$^6$ .................. D04H 1/58; B32B 27/00; D02G 3/00; A61F 13/20
[52] U.S. Cl. .................. 428/288; 428/290; 428/296; 428/369; 428/913; 604/364; 604/365; 604/372
[58] Field of Search .................. 428/288, 290, 475.8, 428/476.3, 483, 507, 511, 514, 520, 913, 286, 287, 369; 128/156, 284, 286, 287, 290, 296

[56] References Cited

U.S. PATENT DOCUMENTS

| | | | |
|---|---|---|---|
| 3,563,241 | 2/1971 | Evans | 428/409 |
| 3,635,221 | 1/1972 | Champaigne, Jr. | 128/290 |
| 3,804,092 | 4/1974 | Tunc | 128/284 |
| 4,117,187 | 9/1978 | Adams et al. | 128/296 |
| 4,242,408 | 12/1980 | Evani et al. | 428/290 |
| 4,362,781 | 12/1982 | Anderson | 428/289 |
| 5,082,720 | 1/1992 | Hayes | 428/369 |

FOREIGN PATENT DOCUMENTS 0326298  10/1993  European Pat. Off. .
WP92/15742  8/1989  WIPO .

OTHER PUBLICATIONS

International Search Report, dated Oct. 11, 1993.
Patent Abstract of Japan; JP2014058, Hiroyuki Kanai, Jan. 18, 1990.
Patent Abstract of Japan; JP1306661, Lion Corp., Dec. 11, 1989.
Database WPI, JP3174417, Lion Corp., Jul. 29, 1991.
Database WPI, JP3239709, Lion Corp., Oct. 25, 1991.
Database WPI: JP63139906, Lion Corp. Jun. 11, 1988.
Database WPI; JP58104902, Yuka Badische KK, Jun. 22, 1983.
Patent Abstracts of Japan; JP2014007, Jan. 18, 1990.

*Primary Examiner*—George F. Lesmes
*Assistant Examiner*—Kathryne E. Shelborne
*Attorney, Agent, or Firm*—Burns, Doane, Swecker & Mathis

[57] ABSTRACT

A water-decomposable non-woven fabric comprises a water-dispersible fiber layer, each fiber of which is bound with one another using a water-soluble binder comprising an unsaturated carboxylic acid/unsaturated carboxylic acid ester copolymer in which 1 to 60 mole % of the repeating units derived from the unsaturated carboxylic acid is in the form of a salt and which is soluble in tap water but is insoluble in an aqueous solution containing not less than 0.5% by weight of a neutral inorganic salt comprising a monovalent ion; the water-dispersible fiber layer being composed of a mixture of 40 to 90% by weight of fibers having a crimp number of 19/inch or less, 10 to 60% by weight of fibers having a crimp number of 20/inch to 25/inch, and not more than 10% by weight of fibers having a crimp number of 26/inch or more; and a content of the binder in the non-woven fabric being 1 to 30% by weight relative to the total weight of the non-woven fabric. The non-woven fabric has a good feeling (high softness and good touch) and sufficient mechanical strength, and can be easily broken and dispersed by throwing into a large amount of water.

11 Claims, No Drawings

WATER-DECOMPOSABLE NON-WOVEN FABRIC

BACKGROUND OF THE INVENTION

The present invention relates to a water-decomposable non-woven fabric which can be easily broken end dispersed by throwing into a large amount of water.

Non-woven fabrics have been widely used as a material for disposable absorbent articles such as sanitary napkins and paper diapers.

The non-woven fabrics used for the absorbent articles must have a toughness sufficient for resisting to breakage when they are wetted with a body fluid such as the menstrual blood or urine. Therefore, water-insoluble resins are generally used as a binder to bind fibers.

On the other hand, it is required of the non-woven fabrics to be used for the disposable absorbent articles or diaper liners that they can be untied into fine pieces and dispersed in water (water-decomposability) so that they can be thrown into a flush toilet. The above-described non-woven fabrics using water-insoluble resins as a binder are, therefore, unsatisfactory in view of these uses.

So far several proposals have been made on the water-decomposable non-woven fabric. For example, Japanese Patent Unexamined Published Application (hereinafter referred to as "J.P. KOKAI") No. Hei 1-306661 discloses a water-decomposable non-woven fabric comprising a water-decomposable fabric layer, each of faber of which is bound with one another using a water-soluble binder mainly containing an unsaturated carboxylic acid/unsaturated carboxylic acid ester copolymer in which a part of the unsaturated carboxylic acid is neutralized to form a salt. In this case, a fiber web is prepared from viscose rayon fibers having a length of 26 mm and a size of 2 denier by airlay method. However, since the viscose rayon fibers employed are or ordinal crimp numbers, i.e., not more than 19/inch, the resulting water-decomposable non-woven fabric has weak mechanical strength. The content of binder in the non-woven fabric was increased in order to increase the mechanical strength, but the resulting non-woven fabric became hard and sufficient mechanical strength could not be obtained, which properties were still unsatisfactory in the practical view points.

SUMMARY OF THE INVENTION

A primary object of the present invention is to provide a non-woven fabric having a good feeling (high softness and good touch), sufficient mechanical Strength and water-decomposability in which the above-described problems in the prior art have been solved.

This and other objects of the present invention will be apparent from the following description and Examples.

After Intensive investigations made for the purpose of solving the above-described problems, the inventors have found that the problems can be solved by using a mixture of specific crimped fibres as a fabric layer of which non-woven fabric is composed and as a result, the present invention has been completed on the basis of this finding.

Namely, the present Invention provides a water-decomposable non-woven fabric comprising a water-dispersible fiber layer, each fiber of which is bound with one another using a water-soluble binder comprising an unsaturated carboxylic acid/unsaturated carboxylic acid ester copolymer in which 1 to 60 mole % of the repeating units derived from the unsaturated carboxylic acid is in the form of a salt and which is soluble in tap water but is insoluble in an aqueous solution containing not less than 0.5% by weight of a neutral inorganic salt comprising a monovalent ion; the water-dispersible fiber layer being composed of a mixture of 20 to 90% by weight of fibers having a crimp number of 19/inch or less, 10 to 60% by weight of fibers having a crimp number of 20/inch to 25/inch, and not more than 10% by weight of fibers having a crimp number of 26/inch or more; and the content of the binder in the non-woven fabric being 1 to 30% by weight relative to the total weight of the non-woven fabric.

DESCRIPTION OF THE PREFERRED EMBODIMENTS

As fibers which compose the water-dispersible fiber layer (also referred to as web), there can be used conventional ones such as natural fibers (e.g. cotton, flax, jute, cotton linter and wooden pulp), regenerated cellulose fibers (e.g. rayon and cupro-ammonium rayon), modified cellulose fibers (e.g. cellulose acetate) and synthetic fibers (e.g. polyvinylalcohol, polyesters, polyamides and polyolefins). Although these fibers can be used singly or in combination, it is advantageous to use natural fibers or cellulose fibers in view of their biodegradabillty.

The web used in the present invention consists of a mixture of crimped fibers having a length of not longer than 30 mm. In this connection, the length of the fiber means a length when the crimped fiber is stretched in straight line. In other words, the length indicates a length of fiber which has not been crimped. The mixture comprises 20 to 90% by weight of fibers having a crimp number of 19/inch or less, 10 to 60% by weight of fibers having a crimp number of 20/inch to 25/inch, and not more than 10% by weight of fibers having a crimp number of 26/inch or more, preferably 60 to 70% by weight of fibers having a crimp number of 19/inch or less, 30 to 40% by weight of fibers having a crimp number of 20/inch to 25/inch, and not more than 5% by weight of fibers having a crimp number of 26/inch or more.

The crimped fibers can be easily prepared by the conventional method and the crimp number thereof can be easily arranged to appropriate numbers by controlling the condition in the preparation. For example, the fibers such as modified cellulose fibers and synthetic fibers can be mechanically crimped by a crimper and the crimp number can be controlled by changing a pressure of the crimper. Further, regarding regenerated cellulose fibers such as rayon, structural anisotropy is given to fibers in the direction of size (width) of the fiber at spinning, cut into short fibers having a certain length, and heated so as to crimp the fibers due to the difference in the heat shrinkage. In this respect, the crimp number can be controlled by changing the structural anisotropy and heating condition such as a temperature and time period.

Where fibers having a length of longer than 30 mm are used and the resulting non-woven fabric is water-decomposed in water, there is observed phenomena in which so-called twined rope is formed by twisting the released fibers with one another. The resulting rope of fibers is of worse flowability and it is difficult to throw it through flush toilet. Therefore, it is preferable that the length of fibers used in the present invention be not longer than 30 mm, more preferably not longer than 20 mm. On the other hand, it is preferable that the length of fibers be not shorter than 5 mm in view of the preparation of the web.

The maximum crimp number of fibers is preferably not more than 30/inch. Where the crimp number is over 30/inch, it tends to easily form a rope of fibers. The minimum crimp number of fibers is preferably not less than 5/inch. Where the crimp number is less than 5/inch, the mechanical strength of the resulting web lowers. It is further preferable to use a mixture of 40 to 90% by weight of fibers having a crimp number of 5/inch to 19/inch and 10 to 60% by weight of fibers having a crimp number of 20/inch to 25/inch.

The web can be prepared by either so-called wet method according to wet paper-making method or so-called dry method according to airlay method or carding method, but the wet method is preferable in view of the resulting web having high softness and good touch. In this connection, the web can be easily prepared even by an ordinal carding method (dry method) since the present invention uses a mixture of the fibers comprising, as a main ingredient, crimped fibers having a crimp number of not more than 25/inch. It is generally believed that it is difficult to prepare a web by a carding method using short fibers of a length of not longer than 30 mm, but the web can be easily prepared from the fibers since the fibers have specific crimp number. The web used as a raw material in the present invention is preferably subjected to water-needling treatment. In this respect, since the specific crimped fibers are used, the water-needling treatment can be easily conducted even under a water pressure of 60 kg/cm$^2$ or lower and non-woven fabric having high softness and good touch can be prepared.

The binders usable in the invention to bind fibers are water-soluble unsaturated carboxylic acid/unsaturated carboxylic acid ester copolymers in which a part of the unsaturated carboxylic acid is neutralized to form a salt and which are soluble in tap water but are insoluble in an aqueous solution containing not less than 0.5% by weight of a neutral inorganic salt comprising a monovalent ion such as NaCl, KCl or NaBr. Although conventional unsaturated carboxylic acids can be used as a monomer component of the copolymers, acrylic acid and/or methacrylic acid are preferable. Examples of the unsaturated carboxylic acid ester monomer components include acrylic esters and/or methacrylic esters having an alkyl group of 1 to 18 carbon atoms or a cycloalkyl group of 3 to 18 carbon atoms and it is preferable that acrylic esters and/or methacrylic esters having an alkyl group of 1 to 12 carbon atoms or a cycloalkyl group of 3 to 12 carbon atoms be used singly or in combination.

More specifically, examples of the copolymers include copolymers of 10 to 90%, preferably 20 to 70% by weight of acrylic acid and/or methacrylic acid and 90 to 10%, preferably 80 to 30% by weight of acrylic esters and/or methacrylic esters having an alkyl group of 1 to 18 carbon atoms or a cycloalkyl group of 3 to 18 carbon atoms in which 2 to 60 mole %, preferably 5 to 50 mole % of acrylic acid and/or methacrylic acid is neutralized to form a salt; or copolymers of 30 to 75%, preferably 40 to 65% by weight of acrylic acid, 5 to 30%, preferably 10 to 25% by weight of acrylic esters and/or methacrylic esters having an alkyl group of 8 to 12 carbon atoms and 20 to 40%, preferably 25 to 35% by weight of acrylic esters and/or methacrylic esters having an alkyl group of 2 to 4 carbon atoms in which 1 to 50 mole %, preferably 2 to 40 mole % of acrylic acid is neutralized to form a salt.

Where the amount of acrylic acid and/or methacrylic acid is larger than the amount mentioned above, strength of the resulting non-woven fabric against body fluids lowers. On the other hand, where the amount of acrylic acid and/or methacrylic acid is smaller than the amount mentioned above, water-solubility of the resulting polymer is reduced. Furthermore, where the neutralized ratio of the unsaturated carboxylic acid is larger than the ratio mentioned above, strength of the resulting non-woven fabric against body fluids lowers. Alternatively, where the neutralized ratio is smaller than the ratio mentioned above, water-solubility of the resulting polymer is reduced. The molecular weight of the copolymers are not particularly limited, although the weight-average molecular weight of the copolymers is preferably 5,000 to 1,000,000, more preferably 30,000 to 500,000.

Any inorganic base or organic base can be optionally used as a neutralizing agent to neutralize the unsaturated carboxylic acid component of the copolymers. Examples of the neutralizing agents include inorganic bases such as sodium hydroxide, potassium hydroxide, lithium hydroxide and sodium carbonate, and amines such as monoethanolamine, diethanolamine, diethylaminoethanol, ammonia, trimethylamine, triethylamine, tripropylamine, morpholine. Preferred are ethanolamines or sodium hydroxide or a combination of potassium hydroxide and ethanolamines.

The water-soluble binders mentioned above can be used singly or in combination with an appropriate amount (preferably not more than 20% by weight relative to total weight of binders) of other water-soluble polymers such as polyvinyl alcohol, polymers of acrylic acid, methacrylic acid or a salt thereof and carboxymethylcellulose.

The binder may be used in such that the non-woven fabric contains 1 to 30%, preferably 2 to 20% by weight of the binder. Where the amount of the binder is less than the amount mentioned above, the resulting non-woven fabric is practically insufficient in view of the mechanical strength. Alternatively, where the amount of the binder is more than the amount mentioned above, the resulting non-woven fabric does not have high softness and good touch.

The binder can be applied to the web by, for example, a spray method, dipping method, printing method or coating method. When the binder is applied to the web, it is possible to uniformly disperse the binder in all area of the web or to disperse in the form of spot. In this respect, it is preferable that some parts in the web remain unbound since the unbound parts work to easily absorb water immersed in the non-woven fabric and to disperse the fabric into each fiber in a short period of time.

Further, absorption and permeability of the non-woven fabric to body fluids can be improved by use of a natural surfactant mild to the skin such as sugar esters, glycerin succinates, alkyl polyglucosides and alkylyglycoside acyl esters in combination with the binder at applying the binder to the web.

Although the basis weight of the non-woven fabric of the present invention is not particularly limited, the basis weight is desirably in the range of 15 to 50 g/m$^2$ which is usually considered to be low.

Even when the non-woven fabric of the present invention is brought into contact with a body fluid such as blood, menstrual blood or urine and wetted with it, the binder is not dissolved therein, since the salt concentration of the body fluid is above the level of dissolution, and the structure of the non-woven fabric is kept to exhibit a toughness and softness satisfactory for the practical use. On the contrary, when the non-woven fabric is brought into contact with water, e.g., tap water, the binder is dissolved, since the salt concentration is reduced to a level low enough for the dissolution of the binder; and the non-woven fabric is easily broken and dispersed in water. Thus the non-woven fabric of the present invention can be thrown into a flush toilet.

The non-woven fabric of the present invention is useful as a surface material or wrapping material for various absorbent articles for absorbing body fluids such as sanitary napkins, sheets for a discharge from the womb, paper diapers and pads for hemorrhoids, or as materials for disposable non-woven fabric products such as bed sheets, toilet sheets for pets and diaper liners which can be thrown into a flush toilet after the use.

The present invention will be illustrated with reference to the following Examples.

REFERENTIAL EXAMPLE 1

47 g of acrylic acid, 53 g of cyclohexyl acrylate, 80 g of ethanol and 50 g of distilled water were fed in a 1000 ml four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.25 g of 2,2'-azobis(2,4-dimethylvaleronitrile) in 20 g of ethanol was added to the resultant solution to initiate the polymerization reaction under heating in a water bath maintained at 80° C. After conducting the polymerization at 80° C. for 6 hours in nitrogen gas stream, the reaction mixture was cooled to room temperature and then neutralized by addition of 24.5 g of 48 wt. % aqueous sodium hydroxide solution and 380 g of distilled water (neutralization rate: 45 molar % based on acrylic acid). The solid content of the resultant polymer solution as determined with a Kett moisture meter was found to be 18.3% and the weight-average molecular weight was 32,000.

REFERENTIAL EXAMPLE 2

55 g of acrylic acid, 15 g of 2-ethylhexyl acrylate, 30 g of butyl acrylate, 110 g of acetone and 30 g of distilled water were fed in a 1000 ml four-necked separable flask provided with a stirrer, reflux condenser and nitrogen-introducing tube to obtain a homogeneous solution. Then nitrogen gas was introduced into the flask through the nitrogen-introducing tube under stirring. 20 minutes after, a solution of a polymerization initiator prepared by dissolving 0.88 g of 2,2'-azobis(2-amidinopropane) dihydrochloride in 10 g of distilled water was added to the resultant solution to initiate the polymerization reaction under heating in a water bath maintained at 70° C. After conducting the polymerization at 70° C. for 6 hours in nitrogen gas stream, the reaction mixture was cooled to room temperature and then neutralized by addition of 7.62 g of 28 wt. % aqueous sodium hydroxide solution and 400 g of distilled water (neutralization rate: 12 molar % based on acrylic acid). The solid content of the resultant polymer solution as determined with a Kett moisture meter was found to be 15.4% and the weight-average molecular weight was 300,000.

EXAMPLE 1

There were used cellulose acetate crimped fibers having a size of 2 denier, length and crimp number shown in Table 1.

The web was prepared by mixing the fibers according to the carding method, subjected to water-needling method under a water pressure of 30 kg/cm² and dried to form the web having a basis weight of 30 g/m².

An aqueous solution containing 3% by weight of the binder prepared by the referential example 1 was applied to the web and dried by the printing method so as to obtain a non-woven fabric having a content of 6% by weight of the binder.

The properties of the non-woven fabrics were examined by the methods described below to obtain the results given in Table 1.

(1) Feeling (softness)

The feeling of the non-woven fabric was evaluated by an organoleptic test and the results were classified into the following three grades:

○: soft,
△: slightly hard (tense), and
x: hard (stiff).

(2) Dry strength

The non-woven fabric was cut to pieces of a size of 2.5 cm×9 cm. The samples thus obtained were tested with a tensile strength tester (Model GAC-100 by Toyo Boldwin Co. Ltd.) at a chuck distance of 5 cm and a stress rate of 100 mm/min.

(3) Wet strength

The samples 2.5 cm×9 cm prepared as described above were immersed in the following artificial urine for 1 minute, taken out therefrom and then dehydrated with a filter paper to a pickup of 150% by weight. The samples thus treated were tested in the same manner as that of the above-described dry strength test.

Formulation of the artificial urine urea 2.0wt %; NaCl 1.0 wt %; CaCl₂ 0.1 wt %; MgCl₂ 0.07 wt %, and a balance of water (4) Water dispersibility 500 ml solution prepared by diluting the artificial urine 200 times with tap water and a piece of the non-woven fabric having a size of 6 cm×6 cm were put in a 1000 ml cylindrical vessel with a lid. The vessel was placed in a shaker and shaken at 300 stroke pep min. The degree of breakage of the non-woven fabric and dispersion thereof in the solution were determined.

3: almost complete dispersion,
2: somewhat insufficient dispersion,
1: no dispersion.

TABLE 1

| Non-woven fabric No. | 1 | 2 | 3* | 4* | 5* | 6 | 7* |
|---|---|---|---|---|---|---|---|
| Fiber 1 length 15 mm crimp n. 7 | | | | | | 35 | 100 |
| Fiber 2 length 15 mm crimp n. 15 | 90 wt % | 40 | 90 | | | | |
| Fiber 3 length 15 mm crimp n. 21 | 10 wt % | 60 | | | 35 | 60 | |
| Fiber 4 length 15 mm | | | | 65 | 5 | | |

TABLE 1-continued

| Non-woven fabric No. | 1 | 2 | 3* | 4* | 5* | 6 | 7* |
|---|---|---|---|---|---|---|---|
| crimp n. 30 Fiber 5 length 35 mm crimp n. 7 | | | | 50 | | | |
| Fiber 6 length 35 mm crimp n. 21 | | | | 10 | 50 | | |
| Feeling | o | o | o | o | o | o | Δ |
| Dry strength (g) | 870 | 960 | 900 | 1060 | 930 | 920 | 500 |
| Wet strength (g) | 380 | 410 | 390 | 450 | 370 | 350 | 180 |
| Water dispersibility | 3 | 3 | 1 | 1 | 1 | 3 | 3 |

Note: crimp n. means crimp number/inch
*shows comparative examples.

As is apparent from Table 1, since the length of the fibers used in the preparation of non-woven fabric Nos. 3 and 4 is too long, the dispersibility thereof is not sufficient, and non-woven fabric No. 5 is also insufficient in terms of dispersibility since the amount of fiber 4 having a high crimp number is too large. The non-woven fabric No. 7 is insufficient in terms of mechanical strength and feeling since the fabric is composed of only fiber 1 having less crimp number. On the other hand, non-woven fabric Nos. 1, 2 and 6 of the present invention are of good properties.

EXAMPLE 2

The web having a basis weight of 30 g/m² was prepared by the same method as in Example 1 except that rayon fibers having a size of 2 denier were used. An aqueous solution containing the binder used in Example 1 was applied to the web and dried so as to obtain a non-woven fabric having a basis weight of about 33 g/m². In this respect, the application of the solution was conducted by a printing method (P), spray method (S) or dipping method (D).

The properties of the resulting non-woven fabrics were determined by the same method in Example 1 and the results are shown in Table 2.

TABLE 2

| Non-woven fabric No. | 1 | 2* | 3 | 4* | 5 | 6 |
|---|---|---|---|---|---|---|
| Fiber 7 length 15 mm crimp n. 7 | 70 wt % | 35 | 70 | 70 | 50 | 70 |
| Fiber 8 length 15 mm crimp n. 23 | 30 wt % | 65 | 30 | 30 | 50 | 30 |
| Application of binder solution | P | P | S | S | D | D |
| Binder content in the non-woven fabric | 6 wt % | 6 | 30 | 35 | 20 | 6 |
| Feeling | o | o | o | X | o | o |
| Dry strength (g) | 850 | 910 | 860 | 1050 | 1180 | 900 |
| Wet strength (g) | 370 | 380 | 320 | 380 | 410 | 400 |
| Water dispersibility | 3 | 1 | 3 | 2 | 3 | 3 |

Note: crimp n. means crimp number/inch
*shows comparative examples.

As shown in Table 2, non-woven fabric No. 4 is inferior in terms of feeling since the content of binder in the fabric is high.

EXAMPLE 3

Rayon fibers (3 denier; length: 10 mm) and water-soluble vinyl alcohol fibers (3 denier; length: 3 mm) were dispersed in water to a fiber concentration of 0.05% by weight with a TAPPI test paper machine and then scooped with a screen to obtain a wet fiber sheet having a dry basis weight of 30 g/m². The sheet was pressed through a felt to squeeze out water from it and dried at a temperature of 90° C. so as to make the vinyl alcohol fibers melt. The resulting sheet was then placed on a 80-mesh plain-weave metal gauze and water-needled with a water needling tester under a water pressure of SO kg/cm².

5 weight % aqueous solution of binder of referential Example 2 was sprayed over the front and back surfaces of the sheet in an each amount of 5% by weight. After drying with a hot air dryer, a water-decomposable non-woven fabric was obtained.

The properties of the resulting non-woven fabrics were determined by the same method in Example 1 and the results are shown in Table 3.

TABLE 3

| Non-woven fabric No. | 1 | 2* |
|---|---|---|
| Rayon 1 length 10 mm crimp n. 7 | 70 wt % | 95 wt % |
| Rayon 2 length 10 mm crimp n. 21 | 25 wt % | 0 |
| PVA length 3 mm crimp n. 5 | 5 wt % | 5 |
| Basis weight | 33 | 33 |
| Feeling | o | Δ |
| Dry strength (g) | 1050 | 890 |
| Wet strength (g) | 310 | 130 |
| Water dispersibility | 3 | 3 |

Note: crimp n. means crimp number/inch
*shows comparative example.

As shown in Table 3, even though the length of the fibers for non-woven fabric No. 1 of the present invention is short as 10 mm, the non-woven fabric could be prepared by a wet method, having good mechanical strength and feeling which are the same as those of the non-woven fabrics of the present invention in Examples 1 and 2. However, since the non-woven fabric No. 2 of the comparative example is composed of a large amount of fibers of crimp number of less than 7/inch, the fabric is practically unsatisfactory in terms of wet strength and feeling.

What is claimed is:

1. A water-decomposable non-woven fabric comprising a water-dispersible fiber layer, each fiber of which is bound with one another using a water-soluble binder consisting essentially of an unsaturated carboxylic acid-/unsaturated carboxylic acid ester copolymer in which 1 to 60 mole % of the repeating units derived from the unsaturated carboxylic acid is in the form of a salt and which is soluble in tap water but is insoluble in an aqueous solution containing not less than 0.5% by weight of a neutral inorganic salt comprising a monovalent ion; the water-dispersible fiber layer being composed of a mixture of 40 to 90% by weight of fibers having a crimp number of 5/inch to 19/inch, 10 to 60% by weight of fibers having a crimp number of 20/inch to 25/inch, and not more than 10% by weight of fibers having a crimp number of 26/inch to 30/inch; and a content of the binder in the non-woven fabric being 1 to 30% by weight relative to the total weight of the non-woven fabric and wherein the fibers have a length of 5 to 30 mm.

2. The water-decomposable non-woven fabric of claim 1 wherein the water-dispersible fiber layer is composed of a mixture of 60 to 70% by weight of fibers having a crimp number of 5/inch to 19/inch, 30 to 40% by weight or fibers having a crimp number of 20/inch to 25/inch, and not more than 5% by weight fibers having a crimp number of 30/inch, 26/inch.

3. The water-decomposable non-woven fabric of claim 1 wherein the water-dispersible fiber layer is composed of a mixture of a mixture of 40 to 90% by weight of fibers having a crimp number of 5/inch to 19/inch and 10 to 60% by weight of fibers having a crimp number of 20/inch to 25/inch.

4. The water-decomposable non-woven fabric of claim 1 wherein the water-soluble binder is a copolymer of 10 to 90% by weight of acrylic acid and/or methacrylic acid and 90 to 10% by weight of acrylic esters and/or methacrylic esters having an alkyl group of 1 to 18 carbon atoms or a cycloalkyl group of 3 to 18 carbon atoms in which 2 to 60 mole % of the repeating units derived from acrylic acid and/or methacrylic acid is in the form of a salt.

5. The water-decomposable non-woven fabric of claim 4 wherein the water-soluble binder is a copolymer of 20 to 70% by weight of acrylic acid and/or methacrylic acid and 80 to 30% by weight of acrylic esters and/or methacrylic esters having an alkyl group of 1 to 18 carbon atom or a cycloalkyl group of 3 to 18 carbon atoms in which 5 to 50 mole % of the repeating units derived from acrylic acid and/or methacrylic acid is in the form of salt.

6. The water-decomposable non-woven fabric of claim 1 wherein the water-soluble binder is a copolymer of 30 to 75% by weight of acrylic acid, 5 to 30% by weight of acrylic esters and/or methacrylic esters having an alkyl group of 8 to 12 carbon atoms and 20 to 40% by weight of acrylic esters and/or methacrylic esters having an alkyl group of 2 to 4 carbon atoms in which 1 to 50 mole % of the repeating units derived from acrylic acid is in the form of a salt.

7. The water-decomposable non-woven fabric of claim 1 wherein the content of the binder in the non-woven fabric is 2 to 20% by weight relative to the total weight of the non-woven fabric.

8. The water-decomposable non-woven fabric of claim 1 wherein the fabric has a basis weight of 15 to 50 g/m$^2$.

9. A water-decomposable non-woven fabric comprising a water-dispersible fiber layer, each fiber of which is bound with one another using a water-soluble binder consisting essentially of an unsaturated carboxylic acid/unsaturated carboxylic acid ester copolymer in which 1 to 60 mole % of the repeating units derived from the unsaturated carboxylic acid is in the form of a salt and which is soluble in tap water but is insoluble in an aqueous solution containing not less than 0.5% by weight of a neutral inorganic salt comprising a monovalent ion; the water-dispersible fiber layer being composed of a mixture of a mixture of 40 to 90% by weight of fibers having a crimp number of 5/inch to 19/inch and 10 to 60% by weight of fibers having a crimp number of 20/inch to 25/inch; the fibers having a length of 5 to 30 mm; a content of the binder in the non-woven fabric being 2 to 20% by weight relative to the total weight of the non-woven fabric; and the fabric having a basis weight of 15 to 50 g/m$^2$.

10. The water-decomposable non-woven fabric of claim 9 wherein the water-soluble binder is a copolymer of 20 to 70% by weight of acrylic acid and/or methacrylic acid and 80 to 30% by weight of acrylic esters and/or methacrylic esters having an alkyl group of 1 to 18 carbon atoms or a cycloalkyl group of 3 to 18 carbon atoms in which 5 to 50 mole % of the repeating units derived from acrylic acid and/or methacrylic acid is in the form of a salt.

11. The water-decomposable non-woven fabric of claim 9 wherein the water-soluble binder is a copolymer of 30 to 75% by weight of acrylic acid, 5 to 30% by weight of acrylic esters and/or methacrylic esters having an alkyl group of 8 to 12 carbon atoms and 20 to 40% by weight of acrylic esters and/or methacrylic esters having an alkyl group of 2 to 4 carbon atoms in which 1 to 50 mole % of the repeating units derived from acrylic acid is in the form of a salt.

* * * * *